United States Patent [19]

Bonnet

[11] Patent Number: 4,685,449
[45] Date of Patent: Aug. 11, 1987

[54] URETERO-RENOSCOPE

[76] Inventor: Ludwig Bonnet, Jahnstrasse 28, 7134 Knittlingen, Fed. Rep. of Germany

[21] Appl. No.: 823,627

[22] Filed: Jan. 29, 1986

[30] Foreign Application Priority Data

Feb. 8, 1985 [DE] Fed. Rep. of Germany ....... 3504252

[51] Int. Cl.$^4$ .............................................. A61B 1/00
[52] U.S. Cl. ...................................................... 128/4
[58] Field of Search ....................................... 128/4–8; 73/151

[56] References Cited

U.S. PATENT DOCUMENTS

| | | | |
|---|---|---|---|
| 1,150,214 | 8/1915 | London | 128/7 |
| 1,705,513 | 3/1929 | Wappler | 128/4 |
| 1,880,551 | 10/1932 | Wappler | 128/7 |
| 2,227,727 | 1/1941 | Leggiadro | 128/6 |
| 2,990,830 | 7/1961 | Hett | 128/4 |
| 3,071,129 | 1/1963 | Wasserman | 128/6 |
| 4,517,962 | 5/1985 | Heckele | 128/6 |
| 4,538,594 | 9/1985 | Boekel et al. | 128/6 |

FOREIGN PATENT DOCUMENTS 3206381  9/1983  Fed. Rep. of Germany .......... 128/4

Primary Examiner—Kyle L. Howell
Assistant Examiner—Max F. Hindenburg
Attorney, Agent, or Firm—Hill, Van Santen, Steadman & Simpson

[57] ABSTRACT

A uretero-renoscope comprises a renoscope shaft and interchangeable first and second optical systems which can be inserted through the shaft and coupled to it at its proximal end. The first optical system has a straight-through objective and is also adapted to allow the passage through it of instruments such as a stone disintegrator. To enable the kidney and/or ureter to be inspected for debris after disintegration of a stone, the first optical system can be withdrawin from the shaft, leaving the shaft in place in the urinary tract, and replaced by a second optical system having a delfected angle of view, suitably of about 70° C. this avoids the necessity of withdrawing and replacing the shaft itself.

3 Claims, 4 Drawing Figures

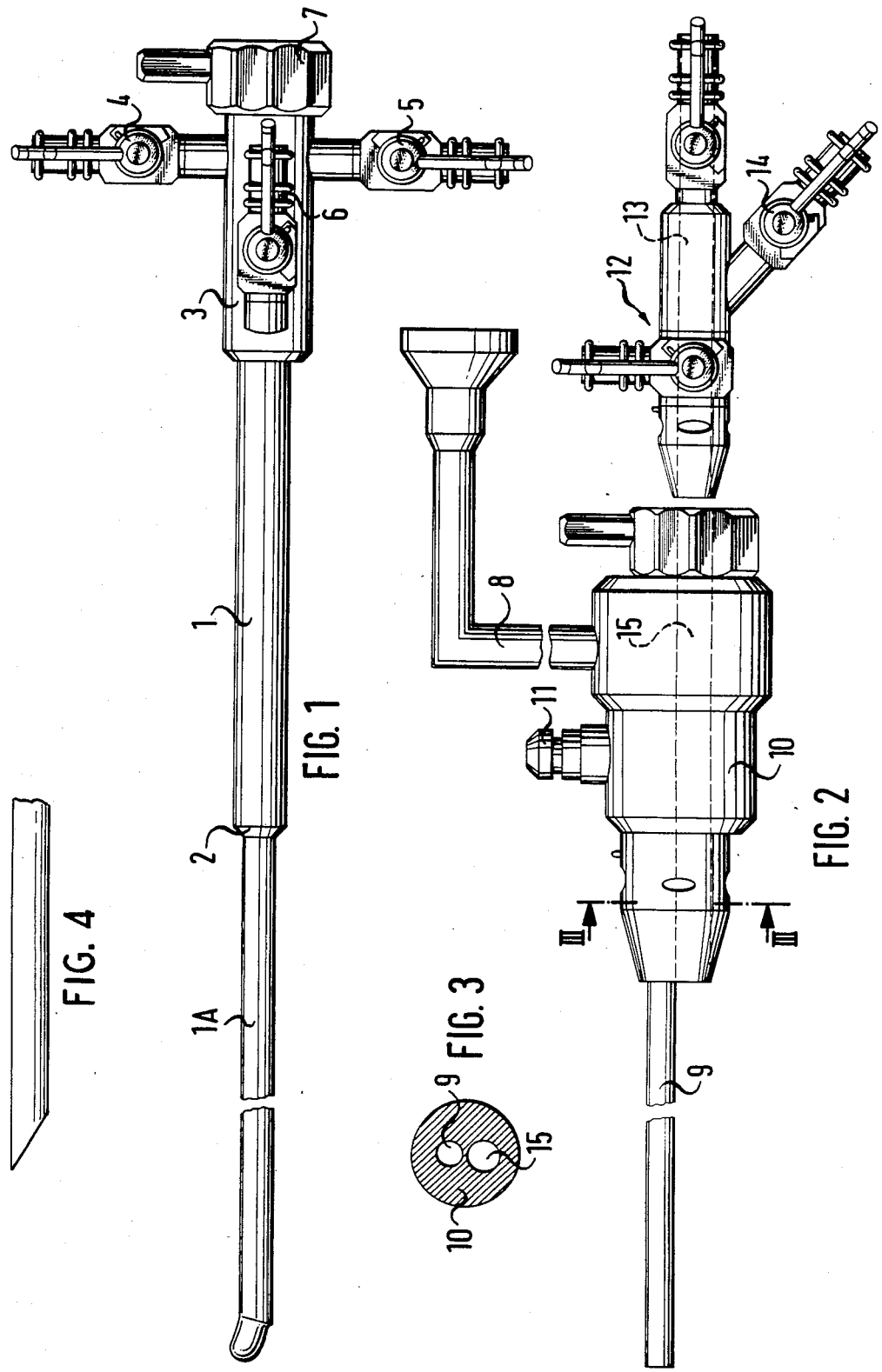

URETERO-RENOSCOPE

BACKGROUND OF THE INVENTION

The invention relates to a uretero-renoscope, the shaft of which is traversed by an optical system having a straight-through objective and an angled eyepiece, and wherein the proximal portion of the optical system casing is provided with a light guide union and an instrument passage for traversal by a stone disintegrator device and of an auxiliary instrument.

DESCRIPTION OF THE PRIOR ART

In the case of ultrasonic lithotripsy of stones, in the urinary tract, visual checks were possible until now only be means of a uretero-renoscope in which the shaft and the optical system form a compact unit having a straight-through objective or foward viewing angle for the optical system. For this reason, it was impossible to make use of the renoscope also for examination of the pelvis of the kidney and of the kidney tegument. A second and compacturetero-renoscope is consequently required for the latter purpose. This examination of the pelvis of the kidney and of the kidney tegument is necessary after a stone disintegration, to ascertain whether stone particles have penetrated into the pelvis or tegument of the kidney, which have to be removed to prevent their forming cores for new stones. For this reason, the whole compact apparatus had to be replaced in use by a second apparatus having a divergent angle of view, so that the compact apparatus having a straight-through objective had to be extracted from the bodily cavity passages and replaced by an apparatus having a divergent angle of view of the optical system, which led to considerable inconvenience to the patient and also required a protracted period of treatment.

SUMMARY OF THE INVENTION

It is an object of the invention to provide a uretero-renoscope assembly which avoids the need for extraction of the whole uretero-renoscope for stone disintegration and subsequent insertion of a second assembly for examination of the pelvis of the kidney or the tegument of the kidney.

According to the invention, this object is achieved in the case of the uretero-renoscope referred to in the foregoing, by the fact that an optical system comprising an elongated optical guide may be coupled as a separate unit into the renoscope shaft, said unit mounting the optical guide eccentrically in the renoscope shaft so that an unobstructed cross-section between the inner surface of the renoscope shaft and the optical guide forms a passage for passing through auxiliary instruments, which leads into a passage of the optical system casing, to which may be coupled an insertion element, which may be of a type known per se and serves at least the purpose of passing through the stone disintegrator device, and that a second optical system is provided, which has a divergent angle of view, advantageously of say 70°, which may be substituted for the optical system having a straight-through objective.

Thanks to this invention solution, the shaft remains constantly in the urinary tract during the examination following a stone disintegration for detection of stone particles in the pelvis of the kidney or in the kidney teguments, and only the optical system coupled to the shaft is released and replaced after its removal by the optical system having a divergent angle of view, to allow unimpeded detection of stone particles.

Other objects and advantageous feature of this invention are described in particular in the following with reference to the accompanying drawings, which show a preferred embodiment of the invention.

BRIEF DESCRIPTION OF THE DRAWINGS

FIG. 1 shows a sideview of a uretero-renoscope according to the invention,

FIG. 2 shows a sideview of the optical system of the uretero-renoscope comprising a proximal insertion element, FIG. 3 shows a cross-section along the line III—III in FIG. 2.

FIG. 4 shows a sideview of the second optical system having a divergent angle of view.

DETAILED DESCRIPTION OF THE PREFERRED EMBODIMENT

The uretero-renoscope according to the invention comprises a shaft 1, which is reduced in diameter by a shoulder 2 along a distal length 1a for insertion into the ureter. The shaft 1 is provided proximally with a casing 3 which is provided with closable connectors 4 and 5 for the inflow and outflow of flushing liquid, and a sloping connector 6 for insertion of an auxiliary instrument, e.g. for holding fast stones which are to be disintegrated. At its proximal end, the casing 3 is provided with a coupling recess and a corresponding clamping ring 7.

An optical system comprising an angled eyepiece 8, a straight-through objective forward viewing angle and an elongated optical guide 9 may be inserted into the shaft 1,3 according to FIG. 1, by placing the optical system casing 10, which is provided with a light source connection stub 11, in engagement in the coupling recess of the shaft housing 3 with the ring 7 engaging a coupler cone of the casing 10. A device for disintegrating stones may be passed through the optical guide which is to be coupled to the shaft 1. To this end, use is advantageously made of an insertion element 12 which may be of a type known per se. The element 12 may be coupled to the optical system casing 10 and has a straight passage 13 as a lead-in for stone disintegration device and an angled passage 14 for traversal by auxiliary instruments, the passages 13, 14 leading into a passage 15 through the optical system casing 10.

After performing a stone disintegration under observation by means of the optical system according to FIG. 2 coupled to the shaft 1, this optical system is freed from the shaft 1, which is left behind in the bodily cavities, by means of which it is possible to examine the pelvis of the kidney and/or the tegument of the kidney with the second optical system having a divergent angle of view.

What is claimed is:

1. A uretero-renoscope assembly comprising a shaft with a longitudinal passage therethrough, a distal portion of said shaft being of a reduced diameter relative to a proximal portion of said shaft, said shaft on a proximal end having a coupler housing, interchangeable first optical system with a forward viewing angle and a second optical system with a divergent angle of view, said first optical system including a casing, an optical guide means being eccentrically mounted in said casing and axially extending from said casing, an angled eye piece extending from said casing and connected to said optical guide means, a light source connector means on said casing, an instrument passage extending through said casing, attachment means for connecting an insertion element to a proximal end of said casing, said instrument passage being open at its end remote to the attachment means to allow at least a stone-disintegration device to be inserted through the instrument passage and be adjacent at distal end of the optical guide means, said first optical system being inserted into the longitudinal passage of the shaft with the casing engaging the coupler housing and the distal end of the optical guide means and the stone-disintegration device carried in said instrument passage extending to the distal end of said shaft, said first optical system being removable from said shaft to allow insertion of the second optical system so that on completion of a stone-disintegration, the second optical system can replace the first system to enable optical examination of the area without removal of the shaft.

2. A uretero-renoscope according to claim 1, wherein said insertion element being releasably connected to the attachment means of the casing of the first optical system.

3. A uretero-renoscope according to claim 1, wherein the coupler housing at the proximal end of the shaft is provided with connectors for an in-flow and out-flow of flushing liquids and a connector to enable insertion of auxiliary instruments into the shaft.

* * * * *